United States Patent [19]

Grey et al.

[11] 4,254,059

[45] Mar. 3, 1981

[54] PROCESS FOR HYDROGENATION OF NITRILES

[75] Inventors: Roger A. Grey, Denville; Guido P. Pez, Boonton, both of N.J.

[73] Assignee: Allied Chemical Corporation, Morris Township, Morris County, N.J.

[21] Appl. No.: 62,874

[22] Filed: Aug. 1, 1979

Related U.S. Application Data

[63] Continuation-in-part of Ser. No. 7,874, Jan. 31, 1979, abandoned.

[51] Int. Cl.$^3$ .............................................. C07C 85/20
[52] U.S. Cl. .................................. 464/492; 260/347.7; 564/415; 564/448; 564/490; 564/491; 564/493; 546/311
[58] Field of Search ............ 260/583 K, 583 P, 570.9, 260/570.8 R; 252/431 P, 431 R

[56] References Cited

U.S. PATENT DOCUMENTS

| | | | |
|---|---|---|---|
| 3,110,747 | 11/1963 | Mullineaux | 260/583 K X |
| 3,152,184 | 10/1964 | Levering | 260/570.9 |
| 3,454,644 | 7/1969 | Dewhirst | 260/570.9 |
| 3,513,200 | 5/1970 | Biale | 260/570.9 X |
| 3,857,900 | 12/1974 | Wilkinson | 260/583 K X |
| 3,878,122 | 4/1975 | Pennella | 252/431 P X |
| 3,957,827 | 5/1976 | Lyons | 252/431 P X |

FOREIGN PATENT DOCUMENTS

| | | | |
|---|---|---|---|
| 2052730 | 5/1971 | Fed. Rep. of Germany | 260/583 P |
| 2062425 | 7/1971 | Fed. Rep. of Germany | 260/583 K |

OTHER PUBLICATIONS

Whitmore et al., "JACS," 66, pp. 725–731 (1944).
Freifelder, "JACS," 82, pp. 2386–2389 (1960).
Band et al., "JACS," 99, pp. 7380–7381 (1977).

*Primary Examiner*—John Doll
*Attorney, Agent, or Firm*—Robert A. Harman

[57] ABSTRACT

A novel process is described for the homogeneous hydrogenation of nitriles to primary amines utilizing anionic Group VIII metal hydride compositions as catalysts which contain phosphorus, arsenic or antimony organoligands. Use of these anionic catalysts allows the high yield hydrogenation of nitriles to primary amines to be conducted under mild conditions of temperature and pressure with high selectivity and eliminates the need for the presence of ammonia to suppress the formation of significant amounts of secondary and tertiary amines.

23 Claims, No Drawings

PROCESS FOR HYDROGENATION OF NITRILES

CROSS REFERENCES TO RELATED APPLICATIONS

This application is a continuation-in-part application of U.S. application Ser. No. 007,874, filed Jan. 31, 1979 now abandoned.

BACKGROUND OF THE INVENTION

1. Field of the Invention

This invention relates to a process for homogeneously hydrogenating nitriles to primary amines under mild conditions utilizing anionic Group VIII metal hydride compositions as catalysts.

2. Brief Description of the Prior Art

The reduction of nitriles is an extremely important industrial process for the production of useful primary amines. For example, adiponitrile is industrially hydrogenated under heterogeneous conditions to yield hexamethylene diamine, which is a well known intermediate in the manufacture of nylon-66 and nylon-610.

Despite the fact that many different processes for the hydrogenation of nitriles are well known and industrially utilized these processes possess certain attendant disadvantages. For example, the references: *J. Am. Chem. Soc.*, 66 pp. 725–731 (1944); U.S. Pat. No. 3,454,644 (1969); *Ger. Offen.* 2,052,730 (1971); *Ger. Offen.* 2,062,425 (1971); and U.S. Pat. No. 3,152,184 (1964) describe catalyzed processes either that require process temperatures above 150° C. or reaction pressures above 150 psig of hydrogen gas in order to achieve adequate yields of primary amines therefrom. These process requirements lead to the disadvantages of the need for expensive apparatus and present special process hazards and require increased energy inputs.

Another process described in *J. Am. Chem. Soc.*, 82, pp. 2386–2389 (1960) which involves low pressure catalytic hydrogenation, requires the presence of significant amounts of ammonia gas during the process to inhibit the formation of secondary amines, thus increasing the overall cost of such process.

The use of nickel clusters as catalysts is described in *J. Am. Chem. Soc.*, 99 pp. 7380–7381 (1977) for reducing nitriles, such as acetonitrile, to amines. However, usually several reduction products are obtained which lowers the yield of the desired amine and presents purification problems.

Due to the large technical and industrial importance of amines, new and improved methods for their manufacture, including that of reduction of nitriles, are constantly being developed. What is desired in the technology of hydrogenating nitriles, is a process which does not require high temperatures, i.e., above 150° C., high pressures, i.e. above 5–7 atmospheres, and which does not require the presence of ammonia for suppression of secondary and tertiary amine formation.

SUMMARY OF THE INVENTION

We have unexpectedly found that the anionic Group VIII metal hydride compositions, described by Guido Pez and Roger Grey in U.S. application Ser. No. 972,147 are very effective catalysts in the hydrogenation of nitriles to primary amines.

The invention process generally involves subjecting a solution of a nitrile and catalyst composition, neat or in a suitable inert solvent, to an atmosphere containing hydrogen gas under mild conditions preferably at temperatures below 150° C. and pressures below 150 psig whereby high yields and high selectivities of the resulting primary amine are obtained. The process does not require high temperature or high pressure or the presence of ammonia to suppress the formation of secondary amines during the hydrogenation of nitriles as do prior art processes.

In accordance with this invention there is provided a process for hydrogenating a nitrile group in a chemical compound to a primary amine group comprising contacting a solution of hydrogenation catalyst and said compound, near or in an inert solvent therefor, with an atmosphere containing hydrogen gas, at a temperature of about 0° to 150° C. under a pressure of about 0 to 150 psig, said catalyst being a composition of the formula:

including dimers, trimers and tetramers thereof, wherein L, L' and L" are independently selected from organoligands containing phosphorus, arsenic or antimony elements, each ligand being free of carbonyl and containing at least one said element, M being a Group VIII metal, H being hydrido, Q being a cation, wherein a, b and c are integer values of 0 or 1, the sum of a, b, c being of from 1 to 3, x being a value of 1 or 2, y being an integer value of from 1 to 3x, x being defined as above, r and s independently being integer values of 1 or 2, and z and q independently being integer values of from 1 to 3, wherein said composition is electrically neutral and contains a minimum of one and a maximum of three atoms of phosphorus, arsenic, antimony, or mixtures thereof, per Group VIII metal atom.

A preferred embodiment of the process is where adiponitrile is hydrogenated to 1,6-diaminohexane comprising contacting a solution of $[(Ph_3P)_3RuH_3]_2^-K^+$ and adiponitrile, neat or in an inert solvent therefor, with an atmosphere containing hydrogen gas, at a temperature of about 0° to 150° C., under a pressure of about 0 to 150 psig.

DESCRIPTION OF INVENTION AND PREFERRED EMBODIMENTS

The novelty of the invention process resides in the fact that the anionic Group VIII metal hydride compositions described in U.S. application Ser. No. 972,147 by Guido Pez and Roger Grey, hereby incorporated by a reference, are very efficient homogeneous catalysts for the hydrogenation of nitriles thus producing the corresponding primary amines. A complete and thorough description of the anionic hydride compositions, their structure, synthesis and physical properties thereof, are adequately described in the above-mentioned reference. For purposes of this invention, the scope of the compositions useful as catalysts in the instant invention process is identical to the scope of the compositions disclosed in the above-described reference. By the terms "hydrogenation catalyst" and "catalyst composition" as used herein, is meant the compositions described above.

The Group VIII metals present in the compositions useful as catalysts in the invention process include iron, cobalt, nickel, ruthenium, rhodium, palladium, osmium, iridium and platinum and preferably ruthenium, rhodium, iron, and platinum, designated as M in the above-described formula.

Organoligands, independently designated L, L' and L", present in the compositions include the coordinating elements phosphorus, arsenic and antimony and preferably those of phosphorus and arsenic. The number of ligands present is 1 to 3 per Group VIII metal atom, designated by the sum of a, b and c, and the value of x, in which each ligand is carbonyl free and contains at least one P, As or Sb element, and included in the total number of ligands, is a maximum of three atoms of said elements present per Group VIII metal atom in the molecule. A maximum of three atoms of P, As or Sb, or mixtures thereof, per Group VIII metal atom is a limitation because it is believed that more than this number interferes in the catalytic process. For example, it has been found by us that when the anionic tris (triphenylphosphine) ruthenium complex, is employed during the homogeneous catalytic hydrogenation of ketones, additional triphenylphosphine has an adverse effect upon catalytic reactivity, wherein we believe the anionic tetrakis(triphenylphosphine) ruthenium complex is formed under the conditions.

It is also considered that carbonyl ligands generally withdraw electronic charge from the respective metal atom, to which they are attached, thus rendering any hydride ligand attached to the metal atom less hydridic in character. Since it is considered that the effectiveness of the subject compositions as homogeneous catalysts is a function of the hydridic nature of the hydride ligands, the subject compositions do not contain carbonyl ligands.

Included among ligands applicable in the compositions are those wherein L, L' and L" are independently of the formulae: (R' R''' $G_1$), (R' R'' R''' $G_1$) or (R' R'' $G_1$—R—$G_2$ R''' R'''') wherein $G_1$ or $G_2$ are independently phosphorus, arsenic or antimony and R', R'', R''' and R'''' are independently selected from $C_1$-$C_{18}$ linear or branched alkyl, phenyl, $C_1$-$C_{18}$ linear or branched alkylphenyl and phenyl-substituted $C_1$-$C_{18}$ linear or branched alkyl, and R being a $C_1$-$C_4$ divalent alkyl bridging group between $G_1$ and $G_2$, wherein said alkyl and phenyl groups can also be substituted with groups inert toward metal arenes, (such as potassium naphthalene) such as $C_1$-$C_4$ alkoxy, being linear or branched, and the like.

Bidentate ligands are considered as being one ligand in the above-described formula for the subject compositions and may form two points of attachment per Group VIII metal atom, or be bridged between two Group VIII metal atoms.

Representative examples of organoligands applicable in the compositions (Ph being used hereinafter to designate phenyl) are triphenylphosphine ($Ph_3P$), diphenylmethylphosphine ($Ph_2CH_3P$), diphenylphosphide ($Ph_2P$), triphenylarsine ($Ph_3As$), diphenylmethylarsine ($Ph_2CH_3As$), trimethylphosphine, triethylphosphine, trioctadecylphosphine, tri-n-octylphosphine, triisopropylphosphine, tri-secondary-butylphosphine, tricyclohexylphosphine, tri(pentamethylphenyl)phosphine, tri(p-tolyl)phosphine, tri(p-n-octadecylphenyl)phosphine, tri(p-n-octylphenyl)phosphine, tri (2-phenethyl) phosphine, tribenzylphosphine, tri(2-phenylisooctadecyl)phosphine, tri(p-methoxyphenyl)phosphine, tri(2-methoxyethyl) phosphine, tri(p-tertiarybutoxyphenyl) phosphine, tri-phenylstibine, dimethylphosphinoethane ($Me_2PCH_2CH_2PMe_2$) and diphenylphosphinoethane ($Ph_2PCH_2CH_2PPh_2$).

Preferred ligands are those of organophosphorus and organoarsine types and particularly preferred are those of organophosphorus, particularly triphenylphosphine, diphenylmethylphosphine and diphenylphosphide.

The charge on the anion in the composition, designated as r, can be $-1$ or $-2$, and the number of anions in the composition, designated by z, can be from 1 to 3.

Cation Q in the composition has a positive charge designated by q from $+1$ to $+3$ and the composition can have from one to three cations, designated by s. Representative examples of cations applicable in the composition include the Group IA alkali metals, such as Li, Na, K, Rb and Cs, the Group IIA alkaline earth metals, such as Be, Mg, Ca, Ba and Sr, Group IIIA metals such as Al, and Ga, divalent and trivalent lanthanide elements such as $La^{+3}$ and $Eu^{+2}$, "metallocene" sandwich-type organo-metallic gegencations, such as $(C_5H_5)_2Ti^+$, and $(C_5H_5)V^+$, and divalent transition metals such as V, Cu, Mn and Fe. Preferred cations in the compositions are $K^+$, $Li^+$, $La^{+3}$ and $V^{+2}$. The total cationic and anionic charges in the compositions are equivalent in absolute value such that the resulting composition is electrically neutral.

The number of hydrogen atoms also termed "hydride" or "hydrido" ligands, attached to the Group VIII metal atoms in the compositions is from 1 to 3x, ("x" being defined above) designated by the symbol y, and can be from 1-6, and preferably two or three. It is believed that where one hydrogen atom is present per two Group VIII metal atoms, the hydrogen atom is bridged between the two respective metal atoms. One of the hydride ligands present can be formed by an ortho-metallation process, described below. The number of hydride ligands is easily established in the molecule by the well-known technique of reacting one gram-mole of said composition in a pure state with at least about one gram-mole of hydrogen chloride, producing about one gram-mole of hydrogen gas per gram-atom of hydrido ligand present in the composition. Stoichiometrically, the reaction requires one gram-mole of hydrogen chloride per hydrido ligand, but in practice a slight excess over this amount is used to insure complete reaction.

Representative examples of subject compositions are illustrated by the following formulas, which are approximate structural formulas as regarded by us on the basis of present available evidence: $[(Ph_3P)_3RuH]^-K^+$; $[(Ph_3P)(Ph_2P)RuH]^-K^+$; $[(Ph_3P)_2RuH]^-K^+$; $[(Ph_2P)_2Fe_2H]=K_2^+$; $[(Ph_3P)_2RuH]^-K^+$; $[(Ph_3P)_3RuH]^-Na^+$; $[(Ph_3P)_3RuH]^-Li^+$; $[(Ph_3P)_3RuH]_2^-Mg^{+2}$; $[(Ph_3P)_2RuH]^{-Li+}$; $[(Ph_3P)_2RuH]^-Cs^+$; $[(Ph_2CH_3P)_3RuH]^-K^+$; $[(Ph_3P)_2PtH]^-K^+$; $[(Ph_3P)_3RhH]^-K^+$; $[(Ph_3P)_2RuH]^-K^+$; $[(Ph_3P)_2RuH_3]^{-K+}$ and $[(Ph_3P)_3RuH_3]_2^-K^+$.

Preferred compositions for use in the process are listed below giving their approximate structural formulas, assigned Roman numerals, used herein for convenient referral thereto, and chemical names.

| Formula | Roman Numerals | Chemical Name |
|---|---|---|
| $[(Ph_3P)_3RuH]^-K^+$ | I | potassium tris(triphenyl phosphine)ruthenium hydride |
| $[(Ph_3P)(Ph_2P)RuH]^-K^+$ | II | potassium triphenylphosphine diphenylphosphide ruthenium hydride |
| $[(Ph_3P)_2RuH]^-K^+$ | III | potassium bis(triphenylphosphine)ruthenium hydride |
| $[(Ph_3P)_3RuH_3]^-K^+$ | IV | potassium bis [tris (triphenylphosphine) |

| Formula | Roman Numerals | Chemical Name |
|---|---|---|
| | | ruthenium trihydride] |

Particularly preferred in the invention process is catalyst composition IV.

The molecular structure of the compositions are fairly complex and have only been rigorously studied in detail in a few cases. For example, structure (I) behaves chemically as a dihydride and, on the basis of its infrared and nuclear magnetic resonance spectra and chemical properties can be more properly presented as being ortho-metallated by the formula:

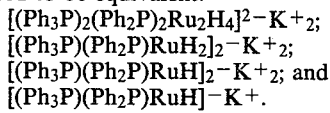

$[(Ph_3P)_2(Ph_2PC_6H_4)RuH_2]^- K^+$

In the case of compound (II) it is felt that orthometallation occurs, but it is not shown in the formula since it is not known which specific phosphine (or phosphide) moiety is in fact ortho-metallated. We have shown that on the basis of chemical reactivity that the compound is a dihydride and also on the basis of proton and $^{31}P$ nuclear magnetic resonance spectra that the compound is a dimer. Thus, for purposes of this disclosure the following approximate structural formula are considered to be equivalent:

$[(Ph_3P)_2(Ph_2P)_2Ru_2H_4]^{2-} K^+{}_2$;
$[(Ph_3P)(Ph_2P)RuH_2]_2{}^- K^+{}_2$;
$[(Ph_3P)(Ph_2P)RuH]_2{}^- K^+{}_2$; and
$[(Ph_3P)(Ph_2P)RuH]^- K^+$.

It is believed that other subject compositions can also exist in dimer, trimer and tetramer forms of their basic empirical formulas.

It is not clearly understood, but is felt that the compositions possess the ability to undergo "ortho-metallation," a process whereby an "unfilled" coordination site on the Group VIII metal atom becomes attached by substitution onto the ortho position of a neighboring phenyl radical as present in triphenylphosphine. The bond formation between the metal atom and the ortho carbon on the phenyl ring displaces the ortho hydrogen bearing a negative charge, i.e. hydride, which then attaches to the metal atom thus forming a dihydride, as indicated by the horizontal bracket in the above described formula. It is considered that "ortho-metallation" in solution, is a dynamic, reversible process in which the ortho-metallated material can react back to the non-ortho-metallated form. This ortho-metallation behavior may be present in the other compositions and can be observed by a dihydride behavior of the substance in that one gram-atom of hydride ligand in the composition in a pure state will liberate one gram-mole of hydrogen gas upon reaction with at least about one gram-mole of hydrogen chloride.

Other chemical characteristics of the compositions are that one gram-atom of hydrido ligand in the composition will liberate one gram-mole of methane upon reaction with at least about one gram-mole of methyl iodide.

The infrared spectra of the compositions exhibit metal-hydride absorption maxima in the infrared region of about 1600 to 2000 cm$^{-1}$ and usually about 1750 to 1950 cm$^{-1}$.

The Group VIII metal hydride compositions applicable herein can be prepared by reacting a neutral Group VIII metal complex, metal halide, hydrido halide or hydride, with a metal cationic radical anion complex, hereinafter referred to as "metal arene," such as potassium naphthalene, or a metal hydride, such as potassium hydride, in a suitable solvent, such as tetrahydrofuran or diethylether, at a temperature of about $-111°$ C. to $+80°$ C., in the case of the metal arene, and $-20°$ to $+150°$ C., in the case of the metal hydride, under an inert atmosphere. The product is easily isolated and purified from the reaction mixture. A description of an apparatus found useful in preparing the composition is described in *J. Amer. Chem. Soc.*, 98, 8072 (1976), hereby incorporated by reference.

The catalyst compositions can exist in the "free form" as described by the above structural formula and can also exist wherein the cation is complexed with an organic solvent in adduct form or as a complex with a chelating agent for said cation. For example, structure (I) can exist as an etherate, being complexed with one mole of diethyl ether per mole of composition. The catalyst composition can also form adducts with aromatic hydrocarbons, such as naphthalene and toluene and chelates with chelating agents, such as crown ethers, e.g., 18-crown-6, cryptates, being bicyclic nitrogen diamines having oxyethylene bridges, such as 2.2.2-crypt, and the like. Adducts and chelates of the compositions, in some cases, display better crystalline properties than the free-form composition, and are more convenient for handling and operability. In addition, the chelated cation may signficantly influence the catalytic activity during hydrogenation due to marked differences in ion-pairing phenomena. However, for purposes of this invention, the free-form composition and adducts and chelates thereof, are considered to be equivalents as compositions and within the scope of applicable compositions.

The products resulting from the hydrogenation of nitriles are primarily the corresponding primary amines obtained in high selectivities although they can be accompanied by very small amounts of up to about 5 molar percent of final products, of secondary and tertiary amines.

Nitriles which are applicable in the invention process are those capable of being hydrogenated to the corresponding primary amines and include the classes of linear or branched saturated aliphatic $C_2$–$C_{18}$ mono- and $C_3$–$C_{18}$ dinitriles and phenyl derivatives thereof, $C_7$–$C_{10}$ saturated alicyclic mononitriles, $C_3$–$C_{10}$ linear or branched olefinically unsaturated aliphatic nitriles, $C_7$–$C_{12}$ aromatic mono- and dinitriles, $C_6$–$C_8$ heterocyclic nitrogen and oxygen mononitriles, $C_3$–$C_4$ cyanoalkanoic amides, $C_2$–$C_4$ saturated aliphatic hydroxynitriles, cyanamide, hydrogen cyanide, or salts thereof, such as sodium, potassium, ammonium, calcium, and the like, or mixtures of the above-described nitriles, wherein said nitriles can also contain non-interfering substituents under the reaction conditions such as $C_1$–$C_4$ alkyl or $C_1$–$C_4$ alkoxy, both being linear or branched.

Representative examples of specific nitriles applicable in the invention process are: [using the "common name" nomenclature, as for example, butyronitrile, being equivalent to butanenitrile (IUPAC) and n-propylcyanide and having the formula, $CH_3(CH_2)_2CN$]; acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lauronitrile ($C_{12}$), tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl cyanide), malononitrile, succinonitrile, glutaronitrile, adiponitrile, acrylonitrile, 3-butenenitrile, 4-pentenenitrile, 2-hexenenitrile, 2-heptenenitrile, glycolonitrile (formaldehyde cyanohydrin) hydracrylonitrile (ethylene cyanohydrin), eqicyanohydrin (gamma-cyanopropylene oxide), lactonitrile, pyruvonitrile, cyclohexane carbonitrile, benzonitrile, o-tolunitrile, m-tolunitrile, p-tolunitrile, anthranilonitrile, m-aminobenzonitrile, p-aminobenzonitrile, 1-naphthonitrile, 2-naphthonitrile, phthalonitrile, isophthalonitrile, terephthalonitrile, mandelonitrile, 2-pyridinenitrile, 3-pyridinenitrile, 4-pyridinenitrile, 2-furyl acetonitrile, cyanamide, hydrogen cyanide, ammonium cyanide, sodium cyanide, potassium cyanide, and calcium cyanide.

Preferred nitriles in the process are acetonitrile, propionitrile, butyronitrile, palmitonitrile, margaronitrile, stearonitrile, malononitrile, succinonitrile, adiponitrile, phenylacetonitrile, benzonitrile, phthalonitrile, terephthalonitrile, acrylonitrile, and 2,2-dimethylpropanenitrile.

Particularly preferred embodiments of the invention process are where acetonitrile is hydrogenated to produce ethylamine, and where adiponitrile is hydrogenated to produce hexamethylenediamine.

Another particularly preferred embodiment is where a linear or branched $C_{16}$–$C_{18}$ saturated aliphatic mononitrile, or mixture thereof, is hydrogenated to produce the corresponding primary amine, or mixture thereof, useful as dispersing agents in the detergent and soap industries.

A still further preferred embodiment is the process for hydrogenating adiponitrile to 1,6-diaminohexane (hexamethylenediamine) comprising contacting a solution of $[(Ph_3P)_3RuH_3]_2^- K^+$ and adiponitrile, neat or in an inert solvent therefor, with an atmosphere containing hydrogen gas, at a temperature of about 0° to 150° C., under a pressure of about 0 to 150 psig.

The primary purpose of the invention process is to hydrogenate the nitrile group in nitrile-containing compounds to the primary amine. However, in some selected instances, other portions of the molecule may also be concomitantly hydrogenated under the reaction conditions. For example, acrylonitrile, will probably be hydrogenated to some extent to propylamine as well as propyleneamine. It is to be understood that we regard the present invention as specifically directed to the hydrogenation of the nitrile group and where other portions of the molecule may also be hydrogenated under the conditions, are not considered to be within the scope of the invention process.

The amount of nitrile substrate present in the process is not critical and is generally about 1 to 100,000 parts by weight per part of catalyst composition, and preferably about 10–1,000 parts by weights per part catalyst. However, larger or smaller amounts of substrate may effectively be used.

The process can be conducted in the neat state, i.e. no solvent, providing the nitrile is liquid at the reaction temperature employed and said hydrogenation catalyst is sufficiently soluble therein to initiate and maintain the hydrogenation reaction. However, it is preferred to conduct the reaction in the presence of an inert solvent for both the nitrile and catalyst composition. The solubility of the respective materials in the solvent should be significantly large enough to initiate and maintain the hydrogenation process.

Solvents which are applicable in the invention process must be inert toward hydrogenation under the reaction conditions and possess adequate solvating ability for the substrate nitrile, and catalyst should preferably be anhydrous, and include $C_6$–$C_{12}$ non-fused benzenoid hydrocarbons, and $C_2$–$C_{18}$ alkyl derivatives thereof, $C_5$–$C_{10}$ linear or branched saturated aliphatic or alicyclic hydrocarbons, $C_4$–$C_6$ saturated aliphatic cyclic mono- or diethers $C_2$–$C_6$ linear or branched saturated aliphatic mono- or diethers, or $C_7$–$C_{14}$ aromatic ethers, or mixtures thereof. By the term "non-fused benzenoid hydrocarbons" is meant that is more than one benzene ring is present in the hydrocarbon, they are isolated and not fused together. Thus, the term includes biphenyl, but not naphthalene.

Representative examples of specific solvents useful in the invention process are xylene, hexamethylbenzene, biphenyl, n-octadecylbenzene, benzene, toluene, pentane, cyclopentane, cyclohexane, methylcyclohexane, hexane, isooctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenylether, and mixtures thereof.

Preferred solvents in the invention process are toluene, benzene, cyclohexane, hexane, tetrahydrofuran, p-dioxane, diethyl ether or 1,2-dimethoxyethane. Particularly preferred solvent is toluene.

The amount of solvent, when used, is not critical provided sufficient solvent is present to dissolve the nitrile substrate and catalyst and to initiate and maintain the hydrogenation reaction. In general, about 1 to 100 parts by weight of solvent per part of nitrile is used, although the amount is not limited thereto, and larger or smaller amounts being also effective with the above proviso.

As described above, the composition catalysts can exist in the free form or can be present as an adduct or chelate with another organic molecule. In cases where increased solubility may be desired of the catalyst composition, as for example when using $C_5$–$C_{10}$ linear or branched saturated aliphatic or alicyclic hydrocarbons, or where rapid reaction rates or higher selectivities towards primary amines are desired, chelating agents of the type described above may be added, such as crown ethers, including 15-crown-5, 18-crown-6, dibenzo and dicyclohexyl derivatives thereof; cryptates, such as 2.2.2-crypt; hexacyclen, the nitrogen analog of 18-crown-6-crown ether; and tertiary amines such as N,N,N',N'-tetramethylethylenediamine and the like. A preferred chelating agent is 18-crown-6. If a chelating agent is used, normally it is used in a molar ratio of chelating agent to catalyst of about 1:1 to 2:1 and preferably in slight excess over the stated 1:1 molar ratio. The use of cation chelating agents, such as the crown ethers, usually results in accelerated rates of the hydrogenation reaction and improved selectivity towards formation of primary amines.

Temperature in the process is normally in the range from about 0° C. to about 150° C. and preferably in the range of about 80° to 100° C. However, higher temperatures under more severe conditions can also be employed and are considered to be equivalent to the stated preferred ranges.

The pressure in the process is usually about 0 to 150 psig at the reaction temperature and preferably about 80 to 100 psig at the reaction temperature. However, higher pressures under more severe conditions can also be employed and are considered to be equivalent to the stated preferred ranges. The term "psig" refers to pounds per square inch gauge, and 0 psig corresponds to 1 atmosphere, and 150 psig corresponds to about 11 atmospheres.

The process is conducted under an atmosphere containing hydrogen gas, being the active reducing agent. The atmosphere above the reaction mixture can also contain an inert gas such as nitrogen, argon, mixtures thereof, and the like as long as sufficient pressure of hydrogen gas is present to maintain the hydrogenation reaction. It is preferred to conduct the process under an atmosphere consisting essentially of hydrogen gas, and particularly preferred at a pressure of about 80–100 psig.

Conversions of nitriles in the process range from about 30 to 100% of theory based on the starting amount of nitrile.

Selectivities in the process for production of primary amines from nitriles are in the range of about 90 to 100%, being defined as (moles primary amine produced/divided by moles nitrile hydrogenated)×100.

Apparatus for conducting the invention process can be any conventional pressure apparatus, glass or steel, in which the operations of charging the reactant materials, heating, cooling, stirring, introduction of hydrogen gas, isolation and purification the final products can be conducted substantially in the absence of air and moisture. Such apparatus and procedure for carrying out the invention process will be obvious to one skilled in the art from this disclosure.

The product primary amine can be isolated from the process and purified by conventional methods such as extraction, fractional distillation or column or gas chromatographic techniques.

The following examples are illustrative of the best mode of carrying out the invention as contemplated by us and should not be construed as being limitations on the scope and spirit of the instant invention.

EXAMPLE 1

A glass pressure tube was charged with 40 mg of of the bisphosphine catalyst, $[Ph_3P)(Ph_2P)RuH_2]_2{}^-K^+{}_2$, prepared by reacting bis(triphenylphosphine)ruthenium hydridochloride toluene with potassium naphthalene in about a 1:2 molar ratio in tetrahydrofuran at about $-80°$ C. under reduced pressure, 0.39 gram gram of acetonitrile and 5 ml of toluene. The reaction solution was pressurized with 90 psig of hydrogen and allowed to react in the absence of moisture and elemental oxygen at 90° C. for 16 hours. Gas chromatographic analysis of the reaction mixture showed 46% conversion of the acetonitrile to a product mixture which consisted of 96% by weight ethylamine and 4% by weight diethylamine.

EXAMPLE 2

The process described in Example 1 was repeated except that 20 mg of 18-crown-6 chelating agent was also initially present during the reaction and the reaction solution was heated at 90° C. for 5 hours under a pressure of 90 psig of hydrogen. Gas chromatographic analysis of the final reaction mixture showed 82% conversion of the acetonitrile to product which consisted of 99% by weight ethylamine.

EXAMPLE 3

Following the procedure described in Example 1, a glass pressure tube was charged with 20 mg of the bisphosphine catalyst described in Example 1, 10 mg of 18-crown-6, 0.4 grams of 2,2-dimethylpropanenitrile and 3 ml of toluene. The reaction solution was pressurized with 90 psig of hydrogen gas and allowed react at 90° C. for 18 hours. Gas chromatographic analysis of the reaction mixture showed 50% reduction of the starting nitrile to a product mixture which consisted of 95% by weight 2,2-dimethylpropylamine and 5% by weight bis (2,2-dimethylpropyl)amine.

EXAMPLE 4

Following the procedure described in Example 1, a glass pressure tube was charged with 20 mg of the bisphosphine catalyst described in Example 1, 10 mg of 18-crown-6, 0.5 grams of benzonitrile and 3 ml of toluene. The reaction solution was pressurized with 90 psig of hydrogen gas and allowed to react at 90° C. for 18 hours. Gas chromatographic analysis of the resulting solution showed 100% conversion to benzylamine with 99% selectivity.

EXAMPLE 5

Following the procedure in Example 1, a glass pressure tube was charged with 40 mg of the bisphosphine catalyst described in Example 1, and 4 grams of acetonitrile. The reaction solution was pressurized with 90 psig of hydrogen gas and allowed to react at 90° C. for 18 hours. Gas chromatographic analysis of the reaction mixture showed 10% conversion to ethylamine as essentially the only hydrogenation product.

EXAMPLE 6

A glass pressure tube was charged with 40 mg of the bis-phosphine catalyst described in Example 1, 20 mg of 18-crown-6, 1 gram of stearonitrile and 3 ml of toluene. The reaction solution was pressurized with 90 psig of hydrogen and allowed to react at 90° C. for 5 hours. Gas chromatographic analysis of the reaction solution showed 100% conversion to stearylamine in a selectivity of about 98%.

EXAMPLE 7

A glass pressure tube was charged with 80 mg of $[(Ph_3P)_3RuH_3]_2{}^-K^+$, (prepared by reacting 5.0 g $[(Ph_3P)_2RuHCl]_2$ toluene complex with 2.5 g dry KH in 140 mL tetrahydrofuran at 20°–25° C. for 5 days under an argon atmosphere) 0.5 g of adiponitrile and 3 mL of toluene. The reaction solution was pressurized with 90 psig of hydrogen and allowed to react at 95° C. for 16 hours. Gas chromatographic analysis of the reaction mixture showed 100% conversion to 1,6-diaminohexane.

EXAMPLE 8

A glass pressure tube was charged with 20 mg of $[(Ph_3P)_3RuH_3]_2{}^-K^+$, as described in Example 7, 0.39 g of acetonitrile and 3 mL of toluene. The reaction solution was pressurized with 90 psig of hydrogen and allowed to react at 90° C. for 16 hours. Gas chromatographic analysis of the reaction mixture showed 100% conversion of the acetonitrile with 97% selectivity to ethylamine.

EXAMPLE 9

The following runs were made utilizing the apparatus and procedure as described in Example 1. The catalyst used was $[(Ph_3P)(Ph_2P)RuH]_2{}^-K_2{}^+$ except where indicated by asterisks, the pressure of hydrogen gas was 90 psig and the temperature in each run was conducted at 90° C. for a period of 18 hours, except where indicated by a double asterisk to denote a 5-hour run. The following table lists the nitrile substrate used, the solvent, chelating agent if used, and calculated N number and selectivity in the process for the product resulting from the hydrogenation.

TABLE

| Substrate | Solvent | Additive | N+ | Selectivity+ (%) |
|---|---|---|---|---|
| Acetonitrile | Toluene | — | 10 | —* |
| " | Toluene | — | 60 | 96 |
| " | THF | — | 90 | 94 |
| " | Toluene | 18-crown-6 | 160 | 99** |
| " | Toluene | hexacyclen | 120 | 98 |
| " | Toluene | 2.2.2-crypt | 60 | 98 |
| Benzonitrile | Toluene | — | 25 | 90 |
| " | Toluene | 18-crown-6 | 160 | 99 |
| 2,2-dimethyl propanenitrile | Toluene | — | 40 | 95 |
| 2,2-dimethyl propanenitrile | Toluene | 18-crown-6 | 80 | 95 |
| Stearonitrile | Toluene | — | 35 | 98 |
| " | Toluene | 18-crown-6 | 55 | 98** |
| Benzylnitrile | Toluene | — | 26 | 98 |

+N = number of moles of primary amine produced per mole of catalyst in one batch reaction run.

*catalyst = $[(PPh_3)_2(Ph_2P\overline{C_6H_4})RuH_2]^-K^+$, 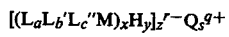
produced by reacting tris (triphenylphosphine) ruthenium hydridochloride with potassium naphthalene in about 1:2 molar ratio in tetrahydrofuran at −80° C. under reduced pressure.
**5 hour run.
+Selectivity in formation of the corresponding primary amine.

We claim:

1. A process for hydrogenating a nitrile group in a chemical compound to a primary amine group comprising contacting a solution of hydrogenation catalyst and said compound, neat or in an inert solvent therefor, with an atmosphere containing hydrogen gas, at a temperature of about 0° to 150° C. under a pressure of about 0 to 150 psig, said catalyst being a composition of the formula:

$$[(L_a L_b' L_c'' M)_x H_y]_z{}^{r-} Q_s{}^{q+}$$

including dimers, trimers and tetramers thereof, wherein L, L' and L" are independently selected from organoligands containing phosphorus, arsenic or antimony elements, each ligand being free of carbonyl and containing at least one said element, M being a Group VIII metal, H being hydrido, Q being a cation, wherein a, b and c are integer values of 0 or 1, the sum of a, b, c being of from 1 to 3, x being a value of 1 or 2, y being an integer value of from 1 to 3x, x being defined above, r and s being independently integer values of 1 or 2, and z and q independently being integer values of from 1 to 3, wherein said composition is electrically neutral and contains a minimum of one and a maximum of three atoms of phosphorus, arsenic, antimony, or mixtures thereof, per Group VII metal atom.

2. The process of claim 1 wherein M is ruthenium, rhodium, iron or platinum.

3. The process of claim 1 wherein L, L' and L" are independently ligands of the formulas:

(R'R"G₁), (R'R"R'''G₁) or
(R'R"G₁—R—G₂R'''R'''')

wherein G₁ and G₂ are independently phosphorus, arsenic or antimony and R', R", R''' and R'''' are independently selected from $C_1$-$C_{18}$ linear or branched alkyl, phenyl, $C_1$-$C_{18}$ linear or branched alkylphenyl and phenyl-substituted $C_1$-$C_{18}$ linear or branched alkyl, and R being a $C_1$-$C_4$ divalent alkyl bridging group.

4. The process of claim 3 wherein L, L', L" are independently organophosphorus or organoarsine ligands.

5. The process of claim 1 wherein said cation is a metal of Group IA, IIA, or IIIA, divalent or trivalent lanthanide element, a metallocene type cation or divalent transition metal.

6. The process of claim 1 wherein said catalyst has the formula:

$$[(Ph_3P)_3RuH_3]_2{}^-K^+.$$ 

7. The process of claim 1 wherein said catalyst has the formula:

$$[(Ph_3P)(Ph_2P)RuH_2]_2{}^-K_2{}^+.$$ 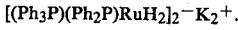

8. The process of claim 1 wherein said catalyst has the formula:

$$[(Ph_3P)_3RuH]^-K^+.$$ 

9. The process of claim 1 wherein said composition is complexed with a chelating agent therefor.

10. The process of claim 9 wherein said chelating agent is 18-crown-6.

11. The process of claim 9 wherein said chelating agent is present in a molar ratio of chelating agent to catalyst of about 2:1 to 1:1.

12. The process of claim 1 further comprising a solvent for said compound and said catalyst.

13. The process of claim 12 wherein said solvent is a $C_6$-$C_{12}$ non-fused benzenoid hydrocarbon, or $C_2$-$C_{18}$ alkyl derivative thereof, $C_5$-$C_{10}$ linear or branched saturated aliphatic or alicyclic hydrocarbon, $C_4$-$C_6$ saturated aliphatic cyclic mono- or diether, $C_2$-$C_6$ linear or branched saturated aliphatic mono- or diether, $C_7$-$C_{14}$ aromatic ether, or mixtures thereof.

14. The process of claim 12 wherein said solvent is toluene, benzene, cyclohexane, hexane, tetrahydrofuran, p-dioxane, diethyl ether or 1,2-dimethoxyethane.

15. The process of claim 1 wherein said compound is present in an amount of about 1 to 100,000 parts by weight of said compound per part of catalyst.

16. The process of claim 1 wherein said temperature is about 80°-100° C.

17. The process of claim 1 wherein said pressure is about 80-100 psig.

18. The process of claim 1 wherein said compound containing a nitrile group is a linear or branched saturated aliphatic $C_2$-$C_{18}$ mono- or $C_3$-$C_{18}$ dinitrile, or phenyl derivative thereof, $C_7$-$C_{10}$ saturated alicyclic mononitrile, $C_7$-$C_{12}$ aromatic mono- or dinitrile, $C_6$-$C_8$ heterocyclic nitrogen or oxygen mononitrile, $C_3$-$C_4$ cyanoalkanoic amide, $C_2$-$C_4$ saturated aliphatic hydroxynitrile, $C_3$-$C_{10}$ linear or branched olefinically unsaturated aliphatic nitrile, cyanamide, or mixture thereof, wherein said nitrile can also contain non-interfering substituents under the reaction conditions.

19. The process of claim 18 wherein said compound is acetonitrile, propionitrile, butyronitrile, palmitonitrile, margaronitrile, stearonitrile, malononitrile, succinonitrile, adiponitrile, phenyl acetonitrile, benzonitrile, phthalonitrile, terephthalonitrile, acrylonitrile, cyanamide, or 2,2-dimethylpropanenitrile.

20. The process of claim 18 wherein said compound is acetonitrile being hydrogenated to ethylamine.

21. The process of claim 18 wherein said compound is a linear or branched saturated aliphatic $C_{16}$–$C_{18}$ mononitrile, or mixture thereof, and the product resulting from the hydrogenation is the corresponding primary amine, or mixture thereof.

22. The process of claim 18 wherein said compound is adiponitrile being hydrogenated to hexamethylenediamine.

23. A process for hydrogenating adiponitrile to 1,6-diaminohexane comprising contacting a solution of $[(Ph_3P)_3RuH_3]_2^-K^+$ and adiponitrile, neat or in an inert solvent therefor, with an atmosphere containing hydrogen gas, at a temperature of about 0° to 150° C. under a pressure of about 0 to 150 psig.

* * * * *